United States Patent [19]
Lloyd et al.

[11] Patent Number: 5,509,404
[45] Date of Patent: Apr. 23, 1996

[54] INTRAPULMONARY DRUG DELIVERY WITHIN THERAPEUTICALLY RELEVANT INSPIRATORY FLOW/VOLUME VALUES

[75] Inventors: Lester J. Lloyd, Orinda; Reid M. Rubsamen, Berkeley, both of Calif.

[73] Assignee: Aradigm Corporation, Hayward, Calif.

[21] Appl. No.: 273,375

[22] Filed: Jul. 11, 1994

[51] Int. Cl.$^6$ .................................................. A61M 11/00
[52] U.S. Cl. .................. 128/200.14; 128/200.23; 128/204.23
[58] Field of Search .................. 128/200.14, 200.23, 128/204.23

[56] References Cited

U.S. PATENT DOCUMENTS

| | | | |
|---|---|---|---|
| 3,187,748 | 6/1965 | Mitchell et al. | 128/200.23 |
| 3,565,070 | 2/1971 | Hamson et al. | 128/200.23 |
| 3,658,059 | 4/1972 | Steil | 128/200.21 |
| 3,812,854 | 5/1974 | Michaels et al. | 128/200.16 |
| 3,814,297 | 6/1974 | Warren | 222/402.13 |
| 3,826,413 | 7/1974 | Warren | 222/402.13 |
| 3,991,304 | 11/1976 | Hillsman | 128/720 |
| 4,484,577 | 11/1984 | Sackner et al. | 128/203.28 |
| 4,592,348 | 6/1986 | Waters, IV et al. | 128/200.23 |
| 4,604,847 | 7/1986 | Moulding, Jr. et al. | 53/75 |
| 4,648,393 | 3/1987 | Landis et al. | 128/200.23 |
| 4,677,975 | 7/1987 | Edgar et al. | 128/200.14 |
| 4,790,305 | 12/1988 | Zoltan et al. | 128/200.23 |
| 4,803,978 | 2/1989 | Johnson, IV et al. | 128/200.23 |
| 4,852,582 | 8/1989 | Pell | 128/716 |
| 4,896,832 | 1/1990 | Howlett | 239/322 |
| 4,926,852 | 5/1990 | Zoltan et al. | 128/200.23 |
| 4,984,158 | 1/1991 | Hillsman | 128/725 |
| 5,363,842 | 11/1994 | Mishelevich et al. | 128/200.23 |

FOREIGN PATENT DOCUMENTS

| | | |
|---|---|---|
| 0232235 | 8/1987 | European Pat. Off. |
| WO92/07599 | 5/1992 | WIPO |
| WO92/15353 | 9/1992 | WIPO |

OTHER PUBLICATIONS

"Recent Progress in Protein and Peptide Delivery by Non-invasive Routes", by Lorraine L. Wearley; Critical Reviews in Therapeutic Drug Carrier Systems, 8(4): 331–394 (1991).
"How Should A Pressurized B–Adrenergic Bronchodilator Be Inhaled?" by Stephen P. Newman et al., Eur. J. Respir. Dis. (1981) 62, 3–21.
Byron, P., *Respiratory Drug Delivery*, 1990, CRC Press, Inc.
Newman, S. et al, "Deposition of pressurised aerosols in the human respiratory tract", 1981, *Thorax*, 36:52–55.
Newman, S. et al., "How should a pressurized β–adrenergic bronchodilator be inhaled?", 1981, *Eur. J. Respir. Dis.*, 62:3–21.
Newman, S. et al., "*Deposition and effects of inhalation aerosols*", 1983.
Newman, S. et al., "Deposition of Pressurized Suspension Aerosols Inhaled Through Extension Devises", 1981, *Am. Rev. Respir. Dis.*, 124:317–320.

Primary Examiner—Aaron J. Lewis
Attorney, Agent, or Firm—Karl Bozicevic; Fish & Richardson

[57] ABSTRACT

A method of drug delivery is disclosed wherein a patient's inspiratory flow rate and inspiratory volume are simultaneously measured using a portable, hand-held, device which may be electronic and battery-powered or mechanical. Information obtained from the measurement is used to release, into a patient's inspiratory flow path, particles of a pharmaceutically active drug. The released particles have a particle size in the range of from about 0.5 to 12 microns. The drug is released when the patient's measured inspiratory flow rate is in the range of from about 0.10 to about 2.0 liters/second and the patient's inspiratory volume is in the range of from about 0.15 to about 0.8 liters. By measuring inspiratory flow and volume and releasing within the specific parameters with respect to both flow and volume, it is possible to obtain a high degree of repeatability with respect to dosing of a patient and further to deliver a relatively high percentage of the released drug to the patient's circulatory system.

30 Claims, 5 Drawing Sheets

INTRAPULMONARY DRUG DELIVERY WITHIN THERAPEUTICALLY RELEVANT INSPIRATORY FLOW/VOLUME VALUES

FIELD OF THE INVENTION

This invention relates generally to methods of intrapulmonary drug delivery and specifically to drug delivery methodology wherein drugs are delivered within specifically defined parameters.

BACKGROUND OF THE INVENTION

The intraputmonary delivery of pharmaceutically active drugs is accomplished by two distinct methodologies. In accordance with one method, a pharmaceutically active drug is dispersed in a low boiling point propellant (a CFC or HFA) and loaded in a pressurized canister from which the drug/propellant formulation may be released by the use of a device generally known as a metered dose inhaler (MDI). Once released, the propellant evaporates and particles of the drug are inhaled by the patient. The other method involves the use of a nebulizer which creates a mist of fine particles from a solution or suspension of a drug which mist is inhaled by the patient. Both methods are hindered by significant problems relating to patient compliance and dosing as described further below.

Metered dose inhalers that are generally manually operated and some breath actuated devices have been proposed and produced. Breath actuated inhalers typically contain a pressurized propellant and provide a metered dose automatically when the patient's inspiratory effort either moves a mechanical lever or the detected flow rises above a preset threshold, as detected by a hot wire anemometer. See, for example, U.S. Pat. Nos. 3,187,748; 3,565,070; 3,814,297; 3,826,413; 4,592,348; 4,648,393; 4,803,978; 4,896,832; and a product available from 3M Healthcare known as Aerosol Sheathed Actuator and Cap.

A major problem with manual metered dose inhalers is that the patient frequently actuates the device at the incorrect point during the breathing cycle to obtain the benefits of the intended drug therapy or breathes at the wrong flow rate. Thus, patients may inspire too little medication, or take additional doses and receive too much medication. The problem is, therefore, the inability to administer precise dosages.

A problem with breath activated drug delivery is that the dose is triggered on crossing a fixed threshold inspiratory effort. Thus, an inspiration effort may be sufficient to release a metered dose, but the inspiratory flow following the release may not be sufficient to cause the aerosol medication to pass into the desired portion of the patient's airways. Another problem exists with patients whose inspiratory effort is not sufficient to rise above the threshold to trigger the release valve at all. Yet another problem is that the velocity and size of the particles released can vary greatly.

Attempts have been made to solve the patient inspiration synchronization problem. U.S. Pat. No. 4,484,577 refers to using a bidirectional reed whistle to indicate to the patient the maximum rate of inhalation for desired delivery of the drug and flow restrictor to prevent the patient from inhaling too rapidly. U.S. Pat. No. 3,991,304 refers to using biofeedback techniques to train the patient to adopt a desired breathing pattern. U.S. Pat. No. 4,677,975 refers to using audible signals and preselected time delays gated on the detection of inspiratory flow to indicate to the patient when to inhale and exhale, and delivering inhalable material a selected time after the detected onset of flow.

Studies in Byron (ed.), *Respiratory Drug Delivery,* CRC Press, Inc. (1990); Newman et al., *Thorax,* 1981, 36:52–55; Newman et al., *Thorax,* 1980, 35:234; Newman et al., *Eur. J. Respir. Dis.,* 1981, 62:3–21; and Newman et al., *Am. Rev. Respir. Dis.,* 1981, 124:317–320 indicate that during a single breath of an aerosol compound, only about ten percent of the total aerosol material presented is deposited into the lungs and that the location of deposition in the lung depends upon (1) breath parameters such as volume of inspiration, inspiratory flow rate, inspiratory pause prior to expiration, the lung volume at the time the bolus of medication is administered, and expiratory flow rate, (2) the size, shape and density of the aerosol particles (i.e., the medicinal compound, any carrier, and propellant), and (3) the physiological characteristics of the patient. Present devices and methods cannot eliminate these variables and as such cannot control dosage administration.

A problem with existing metered dose inhalers, whether or not breath actuated, is that they are factory preset to deliver a fixed dose at a given particle size distribution. Such devices are not capable of reducing the dose to reflect improvement in the patient's condition, or selecting a maximum desired respirable fraction of the aerosol mist that is suitable for a desired location of delivery of the medication in the particular patient.

Devices for controlling particle size of an aerosol are known. U.S. Pat. No. 4,790,305 refers to controlling the particle size of a metered dose of aerosol for delivery to the walls of small bronchi and bronchioles by filling a first chamber with medication and a second chamber with air such that all of the air is inhaled prior to the inhaling medication, and using flow control orifices to control the flow rate. U.S. Pat. No. 4,926,852 refers to metering a dose of medication into a flow-through chamber that has orifices to limit the flow rate to control particle size. U.S. Pat. No. 4,677,975 refers to a nebulizer device that uses baffles to remove from any aerosol particles above a selected size. U.S. Pat. No. 3,658,059 refers to a baffle that changes the size of an aperture in the passage of the suspension being inhaled to select the quantity and size of suspended particles delivered. A problem with these devices is that they process the aerosol after it is generated and thus are inefficient and wasteful.

It is well known that pulmonary functions, such as forced expiratory volume in one second, forced vital capacity, and peak expiratory flow rate, can be measured based on measured flow rates and used to (1) diagnose the existence of medical conditions, (2) prescribe medication, and (3) ascertain the efficiency of a drug therapy program. See, for example, U.S. Pat. Nos. 3,991,304 and 4,852,582 and the publications of Newman et al. discussed above. Heretofore, these tests have been performed using available spirometers. U.S. Pat. No. 4,852,582 also refers to using a peak flow rate meter to measure changes in peak flow rate before and after administration of a bronchodilator. The results of such tests before and after administration of several different medications are used to evaluate the efficiency of the medications.

A problem with the foregoing pulmonary function test devices is that they are too complicated for most patients to use effectively and obtain repeated delivery of a given amount of drug i.e. user error in administration causes significant variability in the amount of drug the patient receives. Another problem is that the data obtained does not directly effect the operation of the device, i.e. it must be examined and interpreted by a trained medical practitioner to be meaningful. Another problem is that they do not provide adequately for altering the dosage of the medication administered in a single patient during the course of therapy, or from patient to patient, using the same delivery device for generating an aerosol of the same or different medications.

Attempts have been made to solve many of the above-referred-to problems. However, inconsistent user compliance combined with undesirably large particle size continues to cause problems with obtaining precise dosing.

Nebulizers utilize various means in order to create a fog or mist from an aqueous solution or suspension containing a pharmaceutically active drug. The mist created by the nebulizer device is directed towards the face of the patient and inhaled through the mouth and nose. Nebulizer devices and methodology can be quite useful when the precise dosing of the drug being delivered to the patient is not of particular importance. For example, in some situations the nebulizer creates a mist from an aqueous solution containing a bronchodilator which can be inhaled by the patient until the patient feels some improvement in lung function. When precise dosing is more important the nebulizer device and delivery methodology suffers from many of the disadvantages of metered dose inhaler devices and methodology as described above. In addition, nebulizers are large in size and not hand-held, easily transportable devices like MDIs. Accordingly, a nebulizer can only be used within a fixed location such as the patient's home, the doctor's office and/or hospital. However, a portable nebulizer is taught in published PCT application WO92/11050 incorporated herein by reference. Another nebulizer which uses a high frequency generator to create an aerosol is described in U.S. Pat. No. 3,812,854 issued May 28, 1974. Drug formulations placed in nebulizers are generally diluted prior to delivery. The entire diluted formulation must generally be administered at a single dosing event in order to maintain the desired level of sterility and the nebulizer cleaned after use. Yet another disadvantage of nebulizers is that they produce an aerosol which has a distribution of particle sizes not all of which are of appropriate size to reach the targeted areas of the lung. The present invention endeavors to address and solve these and other problems.

SUMMARY OF THE INVENTION

The invention provides for the delivery of drugs to the lungs of a human patient in a manner which allows for a high degree of repeatability of dosing and delivery of a high percentage of released drug to the lungs of the patient. The method monitors several parameters and emphasizes measuring a patient's inspiratory flow rate and inspiratory volume simultaneously using a portable, handheld, battery-powered device. Information obtained from the measurement is used to release, into a patient's inspiratory flow path, particles of a pharmaceutically active drug at a given velocity, which particles are within a given size range. The particles have a particle size in the range of from about 0.5 to 12 microns and are preferably released at low velocity relative to inspiration of the patient—most preferably zero velocity. The drug is released when the patient's measured inspiratory flow rate is in the range of from about 0.10 to about 2.0 liters/second and the patient's inspiratory volume is in the range of from about 0.15 to about 0.8 liters. In that the method obtains a high degree of repeatability with respect to dosing of a patient it can be safely and effectively used to deliver a wide range of drugs to a patient's lungs for a topical or local effect and to a patient's circulatory system for a systemic effect.

A primary object of the invention is to provide a method of drug delivery which involves simultaneously measuring a patient's inspiratory flow rate and inspiratory volume and releasing drug into the patient's inspiratory flow path within a specifically measured therapeutically relevant inspiratory flow rate value and inspiratory volume value.

Another object is to provide a method of drug delivery wherein once drug is delivered to a patient at a given inspiratory flow rate and inspiratory volume (both randomly chosen inside the claimed parameters) the drug is released at that point in future releases to insure repeatability of dosing.

An advantage of the invention is that the methodology provides for a high degree of repeatability in dosing a patient via the intrapulmonary route while simultaneously providing to the patient a high percentage of the drug released.

Another advantage of the invention is that the methodology can be carried out on an out-patient basis in that the method is carried out using a portable, hand-held, battery-powered device.

A feature of the invention is that a wide range of different types of drugs and formulations can be delivered to a patient using the basic methodology whereby drug is released within specific inspiratory flow and inspiratory volume parameters.

Another feature of the invention is that by decreasing the amount of released drug which does not reach the patient's lungs the method also decreases the probability that there will be a large percentage of variability in dosing.

These and other objects, advantages and features of the present invention will become apparent to those persons skilled in the art upon reading the present disclosure and reviewing the figures forming a part hereof.

DETAILED DESCRIPTION OF PREFERRED EMBODIMENTS

Figure 1:
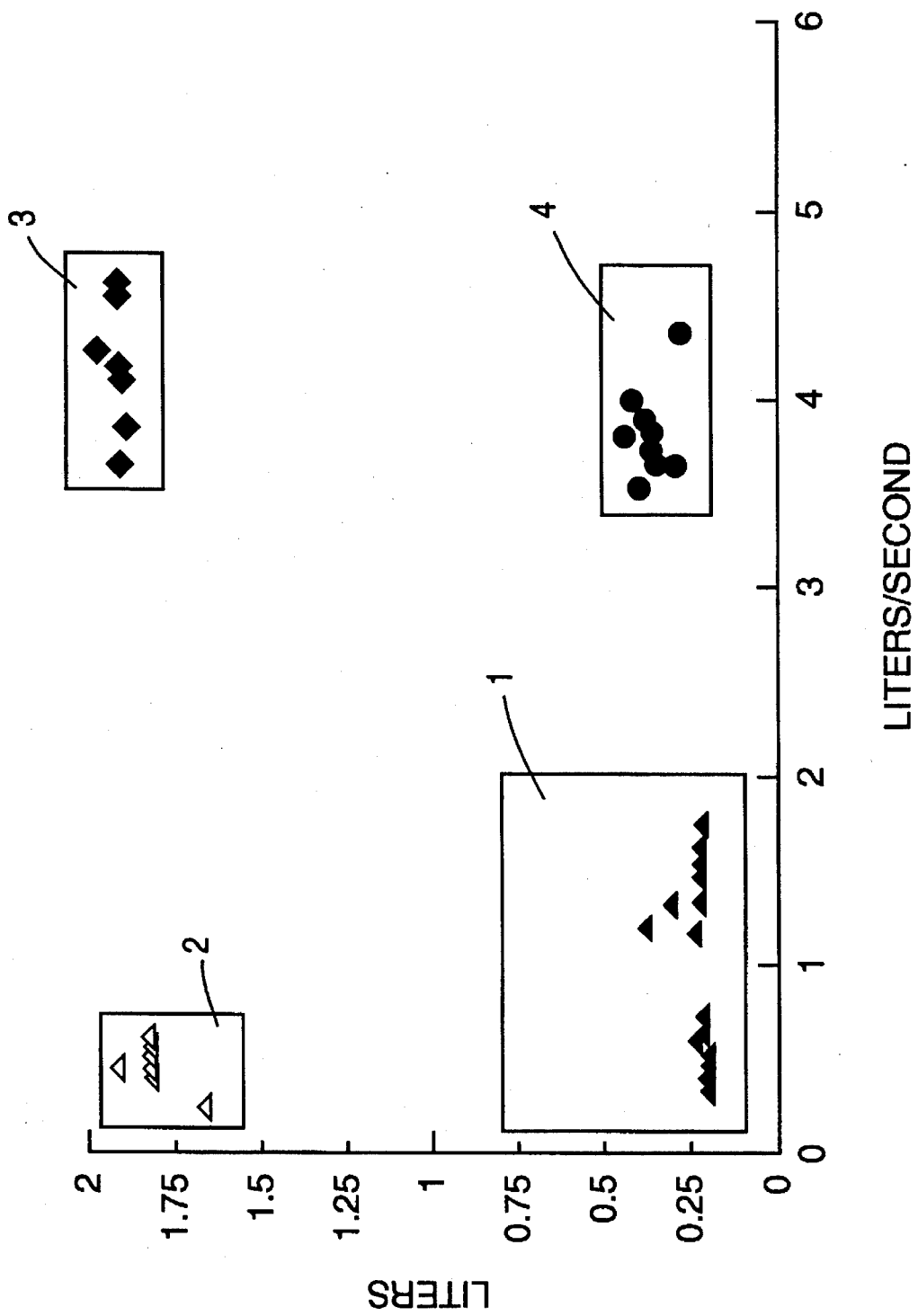
FIG. 1 is a graph showing data points plotted in four general areas with the points plotted relative to inspiratory flow rate (on the abscissa) and inspiratory volume (on the ordinate) in two dimensions.

Before the methodology of the present invention is described, it is to be understood that this invention is not limited to the particular packages, devices, systems, components, and formulations described, as such may, of course, vary. It is also to be understood that the terminology used herein is with the purpose of describing particular embodiments only, and is not intended to limit the scope of the present invention which will be limited only by the appended claims.

It must be noted that as used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth. Although the invention is at times described in connection with specific drugs and formulations it may be used to deliver a wide range of drugs and formulations.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

Definitions

The term "velocity of the drug" shall mean the average speed of particles moving from a drug release point such as a valve to a patient's mouth.

The term "dosing event" shall be interpreted to mean the administration of a pharmaceutically active drug to a patient in need thereof by the intrapulmonary route of administration which event involves the release of drug into the inspiratory flow path of a patient. Accordingly, a dosing event may include the release of drug contained within one or more containers. A dosing event is not interrupted by a monitoring event which would indicate, if followed by further drug delivery, the beginning of a new dosing event.

The term "measuring" describes an event whereby both the inspiratory flow rate and inspiratory volume of the patient is measured in order to determine an optimal point in the inspiratory cycle at which to release aerosolized drug. It is also preferable to continue measuring inspiratory flow during and after any drug delivery and to record inspiratory flow rate and volume before, during and after the release of drug. Such reading makes it possible to determine if drug was properly delivered to the patient.

The term "monitoring" event shall mean measuring lung functions such as inspiratory flow, inspiratory flow rate, and/or inspiratory volume so that a patient's lung function as defined herein, can be evaluated before and/or after drug delivery thereby making it possible to evaluate the efficiency of any treatment.

The term "inspiratory flow rate" shall mean a value of air flow calculated based on the speed of the air passing a given point in a measuring device assuming atmospheric pressure ±5% and a temperature in the range of about 10° C. to 40° C.

The term "inspiratory flow" shall be interpreted to mean a value of air flow calculated based on the speed of the air passing a given point along with the volume of the air that has passed that point with the volume calculation being based on integration of the flow rate data and assuming atmospheric pressure, ±5% and temperature in the range of about 10° C. To about 40° C.

The term "inspiratory flow profile" shall be interpreted to mean data calculated in one or more events measuring inspiratory flow and cumulative volume, which profile can be used to determine a point within a patient's inspiratory cycle which is optimal for the release of drug to be delivered to a patient. An optimal point within the inspiratory cycle for the release of drug is based, in part, on a point within the inspiratory cycle likely to result in the maximum delivery of drug and based, in part, on a point in the cycle most likely to result in the delivery of a reproducible amount of drug to the patient at each release of drug. Repeatability of the amount delivered is the primary criterion and maximizing the amount delivered is an important but secondary criterion. Thus, a large number of different drug release points might be selected and provide for repeatability in dosing provided the selected point is again selected for subsequent releases. To insure maximum drug delivery the point is selected within given parameters.

The term "respiratory drug" shall be interpreted to mean any pharmaceutically effective compound used in the treatment of any respiratory disease and in particular the treatment of diseases such as asthma, bronchitis, emphysema and cystic fibrosis. Useful "respiratory drugs" include those which are listed within the Physician's Desk Reference (most recent edition). Such drugs include beta adrenergics which include bronchodilators including albuterol, isoproterenol sulfate, metaproterenol sulfate, terbutaline sulfate, pirbuterol acetate and salmeterol formotorol; steroids including beclomethasone dipropionate, flunisolide, fluticasone, budesonide and triamcinolone acetonide. Anti-inflammatory drugs used in connection with the treatment of respiratory diseases include steroids such as beclomethasone dipropionate, triamcinolone acetonide, flunisolide and fluticasone. Other anti-inflammatory drugs include cromoglycates such as cromolyn sodium. Other respiratory drugs which would qualify as bronchodilators include anticholenergics including ipratropium bromide. The present invention is intended to encompass the free acids, free bases, salts, amines and various hydrate forms including semi-hydrate forms of such respiratory drugs and is particularly directed towards pharmaceutically acceptable formulations of such drugs which are formulated in combination with pharmaceutically acceptable excipient materials generally known to those skilled in the art— preferably without other additives such as preservatives. Preferred drug formulations do not include additional components which have a significant effect on the overall formulation such as preservatives. Thus preferred formulations consist essentially of pharmaceutically active drug and a pharmaceutically acceptable carrier (e.g., water and/or ethanol). However, if a drug is liquid without an excipient the formulation may consist essentially of the drug which has a sufficiently low viscosity that it can be aerosolized using a dispenser of the present invention.

The term "drug" shall include "respiratory drug" as well as other types of drugs such as systemically effective drugs. The term is intended to encompass the presently available pharmaceutically active drugs used therapeutically and to further encompass to be developed therapeutically effective drugs which can be administered by the intrapulmonary route.

The term "therapeutic index" refers to the therapeutic index of a drug defined as $LD_{50}/ED_{50}$. The $LD_{50}$ (lethal dose, 50%) is defined as the dose of a drug which kills 50% of the animals, and the $ED_{50}$ is defined as the effective dose of the drug for 50% of the individuals treated. Drugs with a therapeutic index near unity (i.e. $LD_{50}/ED_{50}$ is approximately equal to 1) achieve their therapeutic effect at doses very close to the toxic level and as such have a narrow therapeutic window, i.e. a narrow dose range over which they may be administered.

The terms "formulation" and "liquid formulation" and the like are used interchangeably herein to describe any pharmaceutically active drug by itself or with a pharmaceutically acceptable carrier in flowable liquid form and preferably having a viscosity of not more than 25% greater than the viscosity of water. Such formulations are preferably solutions, e.g. aqueous solutions, ethanolic solutions, aqueous/ethanolic solutions, saline solutions and colloidal suspensions. Formulations can be solutions or suspensions of drug in a low boiling point propellant.

The terms "lung function" and "pulmonary function" are used interchangeably and shall be interpreted to mean physically measurable operations of a lung including but not limited to (1) inspiratory and (2) expiratory flow rates as well as (3) lung volume. Methods of quantitatively determining pulmonary function are used to measure lung function. Quantitative determination of pulmonary function is important because lung disease is typically associated with deteriorating pulmonary function. Methods of measuring pulmonary function most commonly employed in clinical practice involve timed measurement of inspiratory and expiratory maneuvers to measure specific parameters. For example, forced vital capacity (FVC) measures the total volume in liters exhaled by a patient forcefully from a deep initial inspiration. This parameter, when evaluated in conjunction with the forced expired volume in one second ($FEV_1$), allows bronchoconstriction to be quantitatively evaluated. A problem with forced vital capacity determination is that the forced vital capacity maneuver (i.e. forced exhalation from maximum inspiration to maximum expiration) is largely technique dependent. In other words, a given patient may produce different FVC values during a sequence of consecutive FVC maneuvers. The FEF 25–75 or forced expiratory flow determined over the mid-portion of a forced exhalation maneuver tends to be less technique dependent than the FVC. Similarly, the $FEV_1$ tends to be less technique dependent than FVC. In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest air flow rate in liters per minute during a forced maximal exhalation, is well correlated with overall pulmonary function in a patient with asthma and other respiratory diseases. The present invention carries out treatment by administering drug in a drug delivery event and monitoring lung function in a monitoring event. A series of such events may be carried out and repeated over time to determine if lung function is improved.

Each of the parameters discussed above is measured during quantitative spirometry. A patient's individual performance can be compared against his personal best data, individual indices can be compared with each other for an individual patient (e.g. $FEV_1$ divided by FVC, producing a dimensionless index useful in assessing the severity of acute asthma symptoms), or each of these indices can be compared against an expected value. Expected values for indices derived from quantitative spirometry are calculated as a function of the patient's sex, height, weight and age. For instance, standards exist for the calculation of expected indices and these are frequently reported along with the actual parameters derived for an individual patient during a monitoring event such as a quantitative spirometry test.

The term "respiratory disease" shall be interpreted to mean any pulmonary disease or impairment of lung function. Such diseases include restrictive and obstructive disease and diseases such as emphysema which involve abnormal distension of the lung frequently accompanied by impairment of heart action. Restrictive diseases tend to limit the total volume of air that a patient is able to exchange through inspiration and expiration. Restrictive disease, such as can be present in certain types of fibrotic processes, can therefore be detected by reduced FVC indices. Obstructive disease, such as is present in patients with asthma, tends not to affect the total volume of air exchangeable through inspiration and expiration but rather the amount of time required for forced exhalation of air. In particular, the $FEV_1$ is markedly reduced in patients with acute asthma symptoms. More specifically, the $FEV_1$, when taken as a ratio of FVC (i.e. $FEV_1$ divided by FVC), is markedly reduced in patients with acute asthma. In addition to increasing the amount of time required for a full forced expiration, the presence of acute bronchoconstrictive disease tends to decrease the peak expiratory flow measured over a typical forced exhalation. The respiratory disease is understood to be "treated" if lung function is improved even if the improvement is temporary.

Method in General

The essential inspiratory parameters of the method of the invention can be described in connection with the attached figures. In particular, FIG. 1 is a two-dimensional graph wherein the inspiratory flow rate is plotted against the inspiratory volume. In developing the invention the patient's inspiratory flow rate and inspiratory volume are simultaneously measured. The measurement is taken and the information obtained from the measurement provided to a microprocessor which microprocessor is programmed to release drug (1) at the same point relative to inspiratory flow and inspiratory volume at each release of drug and (2) to select that point within prescribed parameters of inspiratory flow rates and inspiratory volumes. In the particular results plotted in FIG. 1 the microprocessor was programmed to release drug in four general areas with respect to the inspiratory flow rate and inspiratory volume parameters. This resulted in data points being plotted in four general areas on the two-dimensional graph of FIG. 1. The four areas are labeled 1, 2, 3 and 4. In area 1 (showing solid triangles), the drug was released when the patient's inspiratory flow rate was "slow to medium" (0.10 to 2.0 liters per sec) with an "early" inspiratory volume of 0.15 to 0.8 liters. In area 2 (showing open triangles), the drug was released at a "slow" inspiratory rate/0.10 to 1.0 liters/sec) and a "late" volume (1.6 to 2.8 liters). In area 3 (showing solid diamonds), the drug was released at a "fast" inspiratory flow rate (3.5 to 4.5 liters/sec) and a "late" volume. In area 4 (showing solid circles), the drug was released at a "fast inspiratory flow rate and an "early" inspiratory volume.

The results shown in FIG. 1 were obtained while administering a radioactively labeled drug to a human. After the administration of the drug it was possible to determine not only the amount of drug, but the pattern of drug deposited within the lungs of the patient. Using this information two conclusions were reached. Firstly, it was determined that it is important to simultaneously measure both inspiratory flow rate and inspiratory volume when providing for intrapulmonary drug delivery. Changes in either parameter can greatly effect the amount of drug deposited. Thus, when treating a patient the drug should be released at approximately (±10%, preferably ±5% and most preferable as close as possible to the first release point) the same inspiratory flow rate and inspiratory volume each time—going back to the same point each time for the same patient ensures repeatable dosing. In practice the tighter the point is defined the greater the repeatability of dosing. However, if the point is defined to precisely it can be difficult for the patient to obtain that rate/volume point again. Thus, some degree of tolerance is generally applied. Secondly, it was found that within particular ranges with respect to inspiratory flow rate and inspiratory volume it was possible to obtain a consistently high percentage amount of drug deposited in the lung. Such results are shown graphically within the three dimensional graph as shown in FIG. 2.

Figure 2:
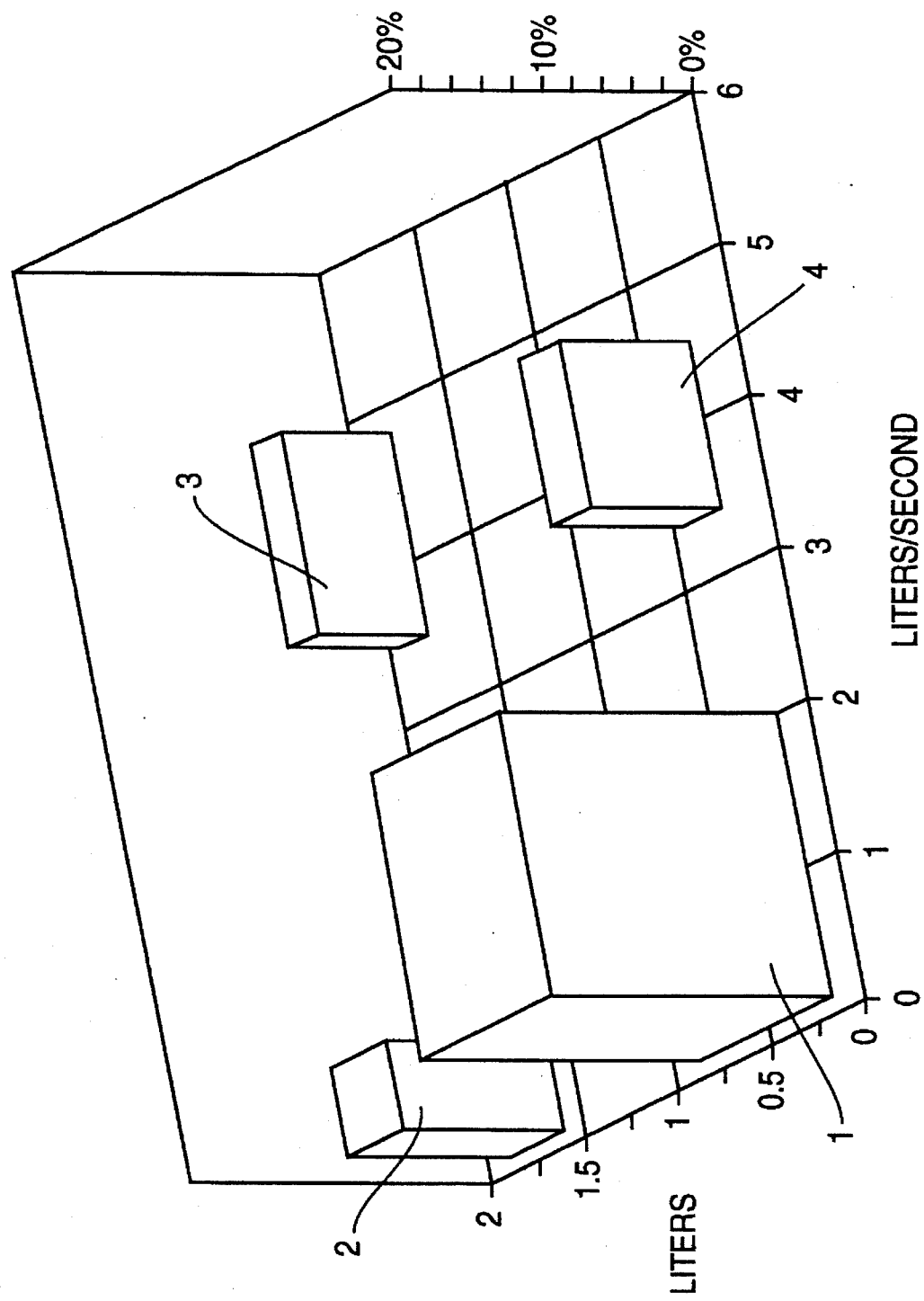
FIG. 2 is a graph showing the four general areas plotted per FIG. 1 now plotted with a third dimension to show the percentage of drug reaching the lungs based on a constant amount of drug released.

The third dimension as shown in FIG. 2 (the height of the four columns) indicates the percentage amount of drug deposited based on the total amount of drug released to the patient. The area labeled 1 clearly showed the highest percentage of drug delivered to the patient based on the amount of drug released. Using this information it was possible to calculate a specific area regarding inspiratory flow rate and inspiratory volume at which it is possible to obtain not only a high degree of repeatability in dosing, but obtain a higher percentage of drug being delivered based on the percentage of drug released. Specifically, it was determined that the drug should be released within inspiratory flow rate range of 0.10 to 2.0 liters per second and at an inspiratory volume in the range of about 0.15 to about 0.80 liters. This range is shown by the rectangularly shaped column of FIG. 3.

In that intrapulmonary drug delivery systems often provide for erratic dosing it is important to provide a method which allows for consistent, repeatable dosing. This is obtained by simultaneously measuring both inspiratory flow rate and inspiratory volume a defining point by its abscissa and ordinate. If both measurements are taken the drug can be released anywhere along the abscissa and ordinate scales shown in FIG. 1. Once a point is selected (such as by randomly selecting a point in box 1 of the graph of FIG. 1) that selected point (with the same coordinants) is used again and again by a given patient to obtain repeatable dosing. If only one parameter is measured (abscissa or ordinate) and drug is released based on that parameter the drug release point is defined by a line on the graph of FIG. 1. When drug is released again the release can be at any point on that line. For example, the inspiratory flow rate (measured horizontally on the abscissa) might be defined by a point. However, the inspiratory volume (which was not measured) would be defined only by a vertical line. Thus, subsequent releases would be at different volumes along that vertical line and the dosing would not be consistent. By measuring both inspiratory flow rate on the abscissa and inspiratory volume on the ordinant the coordinates will mark a point for drug release. That point can be found again and again to obtain repeatability in dosing. The same point should be selected each time as closely as possible and within a margin of errors of ±10% with respect to each criteria. The margin for error can be increased and still maintain acceptable levels of repeatable dosing—but the error should keep the drug release point inside the box 1 of FIG. 1.

By maximizing the amount of released drug which reaches a patient, improved repeatability in dosing is also obtained. This is because there is less of a possibility for a difference in the dosing when nearly all the drug released is administered to the patient. For example, if only 10% of a drug released is actually administered to a patient at one administration the next administration would be ten times as large (1,000% larger) than if 100% of the released drug were administered. However, if a given system administered 80% of the released drug to a patient at one administration the next administration would be only 25% larger than the first if 100% of the released drug were administered. The actual percentage amount of drug delivered will vary from system to system and the above numbers are given only to emphasize a point. The point being that by applying the parameters described herein to any system it is possible to improve the percentage amount of drug administered (based on amount released) and that improvement by itself can improve repeatability of dosing.

Figure 3:
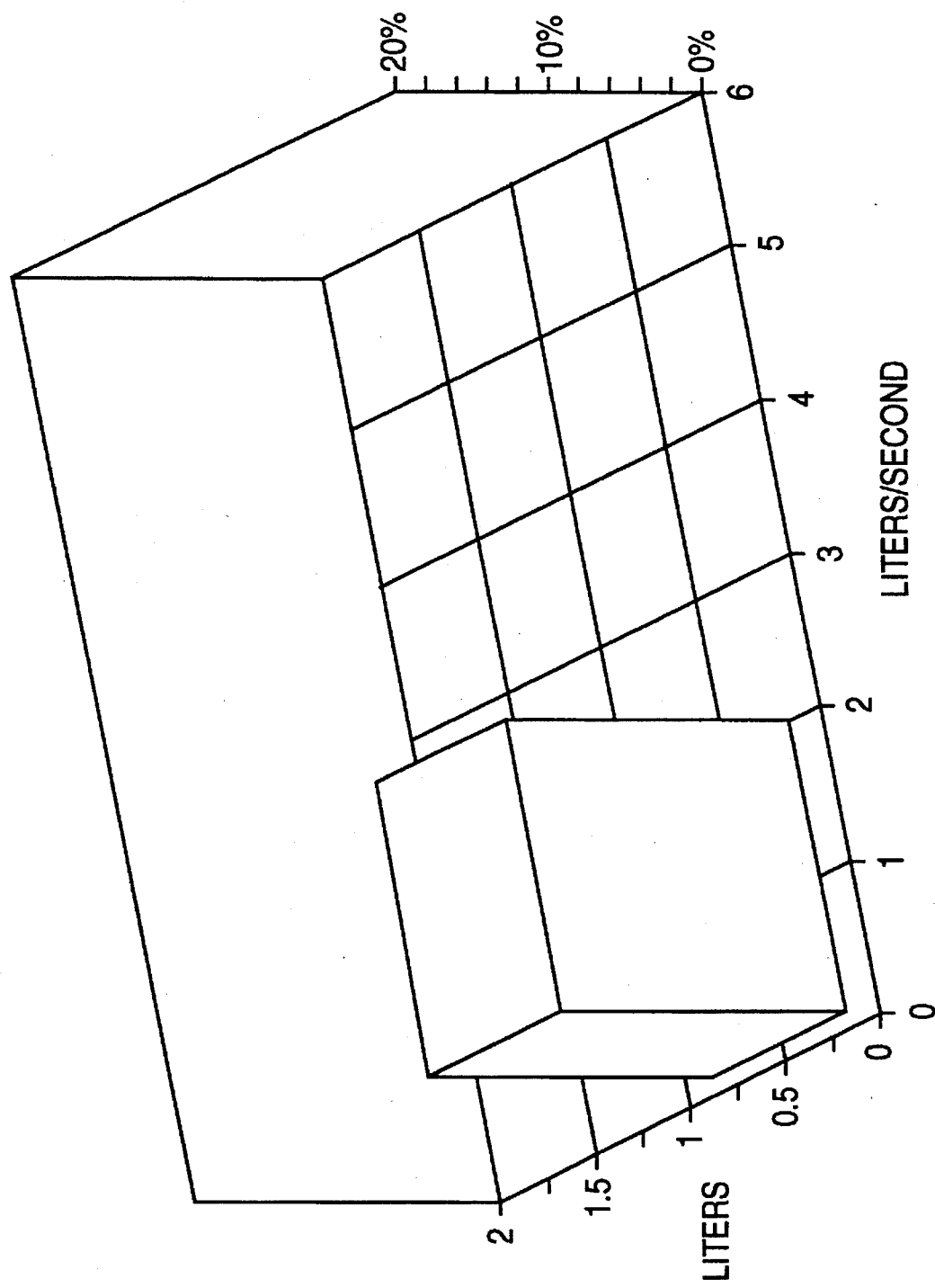
FIG. 3 is a three dimensional graph showing the therapeutic values for inspiratory flow rate and inspiratory volume which provide better drug delivery efficiency.
Figure 4:
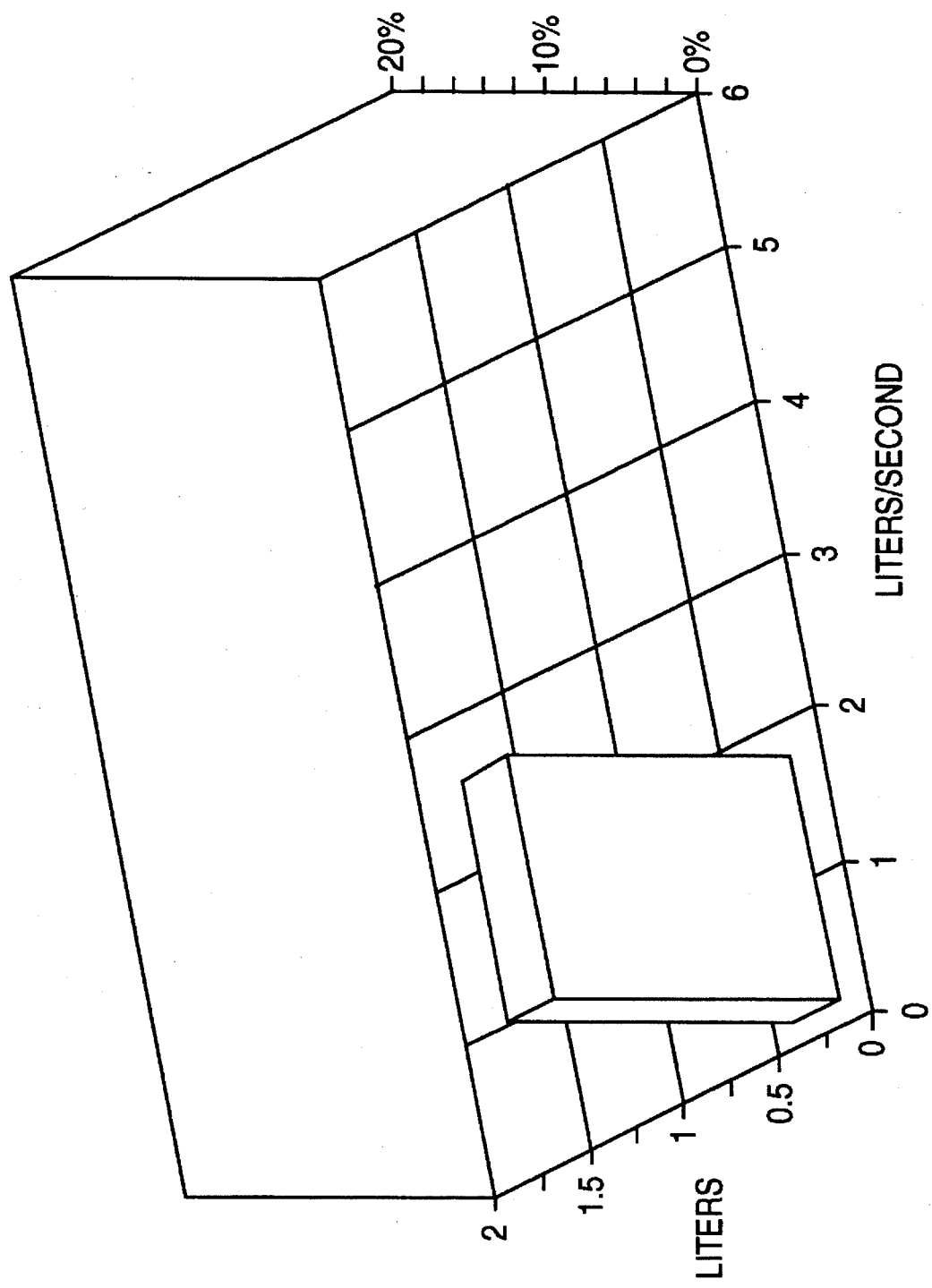
FIG. 4 shows a preferred range of the valves shown in FIG. 3.
Figure 5:
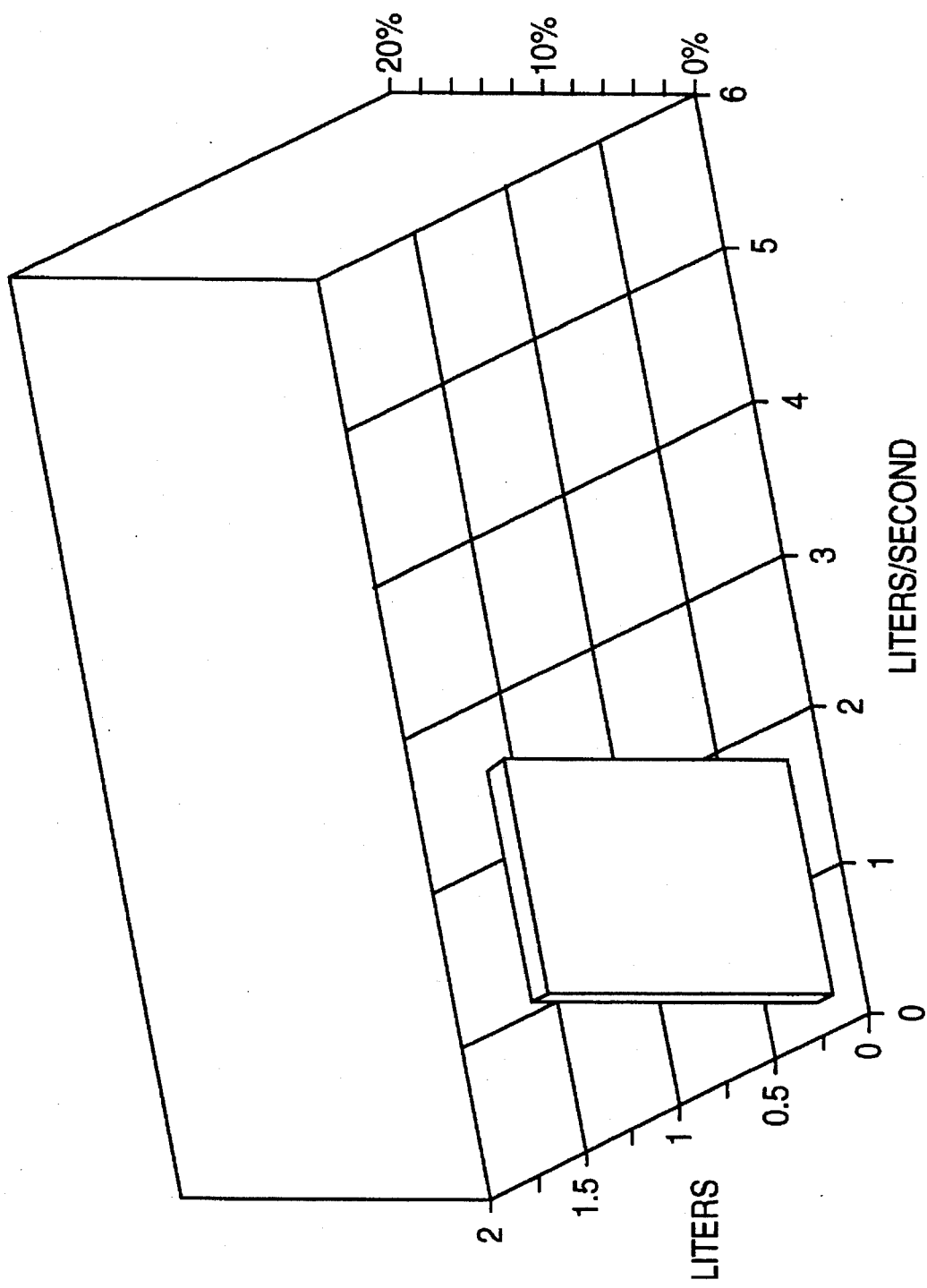
FIG. 5 shown a particularly preferred range for the valves of FIG. 3.

By examining delivery of drug associated with the data points plotted in FIG. 1, it is possible to determine a preferred and particularly preferred and most preferred range as per FIGS. 3, 4 and 5. The preferred range of FIG. 3 shows drug released at a volume of 0.15 to 0.8 liters and rate of 0.10 to 2.0 liters/second. The particularly preferred range plotted in FIG. 4 indicates that the inspiratory flow should be within the range of 0.2 to about 1.8 liters per second with an inspiratory volume in the range of 0.15 to about 0.4 liters. The most preferred range (FIG. 5) is from about 0.15 to about 1.8 liters per second for the inspiratory flow rate and about 0.15 to about 0.25 liters for the inspiratory volume. Thus, the essence of the invention is (1) repeatedly delivering aerosolized drug to a patient at the same simultaneously measured inspiratory flow rate and inspiratory volume and (2) releasing drug to the patient within specified therapeutically effective ranges as shown within FIGS. 3, 4 and 5. The invention involves releasing drug (after measuring) inside the ranges as per FIGS. 3, 4 or 5. Thus, the release could begin inside or outside the range. Preferable the drug release begins inside the range and more preferable begins and ends inside the ranges of FIGS. 3, 4 or 5.

The methodology of the invention is preferably carried out using a portable, hand-held, battery-powered device. As per U.S. patent application Ser. No. 08/002,507 filed Jan. 29, 1993 incorporated herein by reference. Alternatively, the methodology of the invention could be carried out using a mechanical (non-electronic) device. Those skilled in the art recognized that various components can be mechanical set to actuate at a given inspiratory flow rate (e.g. a spring biased valve) and at a given volume (e.g. a spinable flywheel which rotates a given amount per a given volume). The components of such devices could be set to allow drug release inside the parameters of FIGS. 3, 4 or 5.

The drug which is released to the patient may be in a variety of different forms. For example, the drug may be an aqueous solution of drug, i.e., drug dissolved in water and formed into small particles to create an aerosol which is delivered to the patient. Alternatively, the drug may be in a solution wherein a low-boiling point propellant is used as a solvent. In yet, another embodiment the drug may be in the form of a dry powder which is intermixed with an airflow in order to provide for particlelized delivery of drug to the patient. Regardless of the type of drug or the form of the drug formulation, it is preferable to create drug particles having a size in the range of about 0.5 to 12 microns. By creating drug particles which have a relatively narrow range of size, it is possible to further increase the efficiency of the drug delivery system and improve the repeatability of the dosing. Thus, it is preferable that the particles not only have a size in the range of 0.5 to 12 microns but that the mean particle size be within a narrow range so that 80% or more of the particles being delivered to a patient have a particle diameter which is within ±20% of the average particle size, preferably ±10% and more preferably ±5% of the average particle size.

The velocity at which the aerosolized drug is released to the patient is also important in terms of obtaining a high degree of repeatability in dosing and providing for a high percentage of drug being delivered to the patient's lungs. Most preferably, the drug is released from a container in a direction which is normal to the patient's airflow. Accordingly, the drug may be released directly upward so that its flow is at a 90° angle with respect to the patient's inspiratory flow which is directly horizontal. After being released, the drug velocity decreases and the drug particles remain suspended for a sufficient period of time to allow the patient's inspiration to draw the drug into the patient's lungs. The velocity of drug released in the direction from the drug release point to the patient may match the patient's inspiratory flow rate but is preferably slower that the patient's inspiratory flow rate and is most preferably about zero. The velocity may be slightly negative, i.e., in a direction away from the patient. The velocity may range from −2.0 liters/sec to 2.0 liters/sec and is preferably zero. It is not desirable to project the drug toward the patient at a rate above the speed of the patient's breath as such may result in drug being deposited on the back of the patient's throat. Thus, the drug release speed should be equal to or less than the breath speed. The actual speed of release can vary depending on factors such as the particle size, the particle composition and the distance between the point of release and the patient. The velocity is preferably such that the particles will (due to air resistance) slow to zero velocity after traveling a distance of about 2 centimeters or less. In general, the shorter the distance required to slow the particles to zero velocity the better.

An aerosol may be created by forcing drug through pores of a membrane which pores have a size in the range of about 0.25 to 6 microns. When the pores have this size the particles which escape through the pores to create the aerosol will have a diameter in the range of 0.5 to 12 microns. Drug particles may be released with an air flow intended to keep the particles within this size range. The creation of small particles may be facilitated by the use of the vibration device which provides a vibration frequency in the range of about 800 to about 4000 kilohertz. Those skilled in the art will recognize that some adjustments can be made in the parameters such as the size of the pores from which drug is released, vibration frequency, pressure, and other parameters based on the density and viscosity of the formulation keeping in mind that the object is to provide aerosolized particles having a diameter in the range of about 0.5 to 12 microns.

The drug formulation may be a low viscosity liquid formulation which is preferably a formulation which can be aerosolized easily and includes respiratory drug formulations currently used in nebulizers. The viscosity of the drug by itself or in combination with a carrier must be sufficiently low so that the formulation can be forced out of openings to form an aerosol, e.g., using 20 to 200 psi to form an aerosol preferably having a particle size in the range of about 0.5 to 12 microns.

Drug may be stored in and/or released from a container of any desired size. In most cases the size of the container is not directly related to the amount of drug being delivered in that most formulations include relatively large amounts of excipient material e.g. water or a saline solution. Accordingly, a given size container could include a wide range of different doses by varying drug concentration. The amount of drug delivered to the patient will vary greatly depending on the particular drug being delivered. In accordance with the present invention it is possible to deliver a wide range of different drugs. For example, drugs included within the container could be drugs which have a systemic effect such as narcotic drugs, for example fentanyl, sufentanil, or anxiolytic drugs such as diazepam midazolam as well as peptide drugs, e.g. insulin and calcitonin. In addition, mixed agonist/antagonist drugs such as butorphanol can also be used for the management of pain delivered to provide relief from pain or anxiety. However, in that the drugs are delivered directly to the lungs, respiratory drugs are included and include proteins such as DNAse. The preferred respiratory drugs are albuterol, beclomethasone dipropionate, triamcinolone acetonide, flunisolide, cromolyn sodium, and ipratropium bromide, and include, free acids, bases, salts and various hydrate forms thereof generally administered to a patient in an amount in the range of about 50 µg–10,000 µg. These doses are based on the assumption that when intrapulmonary delivery methodology is used the efficiency of the delivery is approximately 10% and adjustments in the amount released must be made in order to take into account the efficiency of the device.

Drug containers may include indices which may be electronic and may be connected to a power source such as a battery. When the indices are in the form of visually perceivable numbers, letters or any type of symbol capable of conveying information to the patient. Alternatively, the indices may be connected to a power source such as a battery when the indices are in the form of magnetically, optically or electronically recorded information which can be read by a drug dispensing device which in turn provides visual or audio information to the user. The indices can be designed for any desired purpose but in general provides specific information relating to the day and/or time which the drug within a container should be administered to the patient. Such indices may record, store and transfer information to a drug dispensing device regarding the number of doses remaining in the container. The containers may include labeling which can be in any format and could include days of the month or other symbols or numbers in any variation or language.

In addition to disclosing specific information regarding the day and time for drug delivery the indices could provide more detailed information such as the amount of drug dispensed from each container which might be particularly useful if the containers included different amounts of drug. Further, magnetic, optical and/or electronic indices could have new information recorded onto mhem which information could be placed there by the drug dispensing device. For example, a magnetic recording means could receive information from the drug dispensing device indicating the precise time which the drug was actually administered to the patient. In addition to recording the time of delivery the device could monitor the expected efficacy of the delivery based on factors such as the inspiratory flow rate which occurred following the initial release of drug. The information recorded could then be read by a separate device, interpreted by the care-giver and used to determine the usefulness of the present treatment methodology. For example, if the patient did not appear to be responding well but the recorded information indicating that the patient had taken the drug at the wrong time or that the patient had misdelivered drug by changing inspiratory flow rate after initial release it might be determined that further education in patient use of the device was needed but that the present dosing methodology might well be useful. However, if the recordings indicated that the patient had delivered the drug using the proper techniques and still not obtained the correct results a different drug or dosing methodology might be recommended.

The method of the invention is preferably carried out using a hand-held, portable device comprised of (a) a device for holding a disposable package comprised of at least one but preferably a number of drug containers, (b) a propellant or a mechanical mechanism for forcing the contents of a container from a porous membrane (c) a monitor for analyzing the inspiratory flow, rate and volume of a patient, and (d) a switch for automatically releasing or firing the mechanical means after the inspiratory flow and/or volume reaches a threshold level. The device may also include a transport mechanism to move the package from one container to the next. The entire device is self-contained, light weight (less than 1 kg preferably less than 0.5 kg loaded) and portable.

The device may include a mouth piece at the end of the flow path, and the patient inhales from the mouth piece which causes an inspiratory flow to be measured within the flow path which path may be in a non-linear flow-pressure relationship. This inspiratory flow causes an air flow transducer to generate a signal. This signal is conveyed to a microprocessor which is able to convert, continuously, the signal from the transducer in the inspiratory flow path to a flow rate in liters per minute. The microprocessor can further integrate this continuous air flow rate signal into a representation of cumulative inspiratory volume. At an appropriate point in the inspiratory cycle, the microprocessor can send a signal to an actuation means and the vibration device below the resonance cavity. When the actuation means is signaled, it causes the mechanical means to force drug from a container on the package into the inspiratory flow path of the device and ultimately into the patient's lungs. After being released, the drug and carrier will pass through a porous membrane which is vibrated to aerosolize the formulation and thereafter the lungs of the patient. Containers and systems of the type described above are disclosed and described in U.S. patent application Ser. No. 08/247,012 filed May 20, 1994 which is incorporated herein by reference.

It is important to note that the firing threshold of the device is not based on a single criterion such as the rate of air flow through the device or a specific time after the patient begins inhalation. The firing threshold is based on an analysis of the patient's inspiratory flow profile. This means that the microprocessor controlling the device takes into consideration the instantaneous air flow rate as well as the cumulative inspiratory flow volume. Both are simultaneously considered together in order to determine the optimal point in the patient's inspiratory cycle most preferable in terms of (1) reproducibly delivering the same amount of drug to the patient with each release of drug by releasing drug at the same point each time and maximizing the amount of drug delivered as a percentage of the total amount of drug released by releasing with the parameters described herein.

The device preferably includes a means for recording a characterization of the inspiratory flow profile for the patient which is possible by including a microprocessor in combination with a read/write memory means and a flow measurement transducer. By using such devices, it is possible to change the firing threshold at any time in response to an analysis of the patient's inspiratory flow profile, and it is also possible to record drug dosing events over time. In a particularly preferred embodiment the characterization of the inspiratory flow can be recorded onto a recording means on the disposable package.

It is important to note that a variety of devices can be used in order to carry out the methodology (including the respiratory disease treatment methodology) of the present invention. However, the device must be capable of simultaneously measuring inspiratory flow rate and volume and sending the measured results to a microprocessor which determines release of drug can occur and sending a drug release signal (all electronically and via the microprocessor). The details of a drug delivery device which includes a microprocessor and pressure transducer of the type used in connection with the present invention are described and disclosed within U.S. patent application Ser. No. 07/664,758, filed on Mar. 5, 1991 entitled "Delivery of Aerosol Medications for Inspiration" which application is incorporated in its entirety herein by reference, and it is specifically incorporated in order to describe and disclose the microprocessor and program technology used therewith. (See also PCT application 92-01815 also incorporated by reference.) The use of such a microprocessor with a drug delivery device is disclosed in our earlier filed U.S. application Ser. No. 08/065,660 filed May 21, 1993 incorporated herein by reference. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, a microprocessor, containing read only memory which in turn contains the pre-programmed information, is plugged into the device. For each of these three embodiments, changing the programming of the memory device readable by a microprocessor will radically change the behavior of the device by causing the microprocessor to be programmed in a different manner. This is done to accommodate different drugs for different types of treatment.

Microprocessor sends signals via an electrical connection to electrical actuation device which actuates a mechanism releasing drug held under pressure or forcing drug formulation in a container to be aerosolized so that an amount of aerosolized drug is delivered into the patient's inspiratory flow path. Further, the microprocessor keeps a record of all drug dosing times and amounts using a read/write nonvolatile memory which is in turn readable by an external device. Alternatively, the device records the information onto an electronic or magnetic strip on the drug container. The recorded information can be read later by the care-giver to determine the effectiveness of the treatment. In order to allow for ease of use, it is possible to surround the patient's inspiratory flow path with a mouth piece.

In a preferred embodiment of the methodology of the invention several different criteria are considered. (1) The inspiratory flow rate and inspiratory volume are simultaneously measured to insure repeatability. (2) The drug is released inside the parameters of FIGS. 3, 4 or 5 with FIG. 5 parameters being most preferred. (3) The particle size of the released drug is in the range of 0.5 to 12 microns and 80% or more and the particles have the same size as the average particle size ±10% in size. (4) The drug particles are released at a velocity which is obtained at a flow rate in the range of greater than −2.0 liters/sec. and less than 2.0 liters/sec. As indicated early the actual velocity can vary based on a number of factors. The release velocity should be determined so that the particles are at or are slowed to zero velocity after traveling about 0.5 to 2 cm from the release point. The speed being measured from the drug release point in a direction toward the back of the throat of the patient.

After dosing a patient with a systemic drug it is desirable to take blood samples and make adjustments as needed to obtain the desired drug to blood ratio. When delivering respiratory drugs it is desirable to measure lung functions over time to determine the effect of the treatment. In accordance with all methods the patient does not push a button to release drug. The drug is released automatically by signals from the microprocessor using measurements obtained.

The electrical actuation means is in electrical connection with the microprocessor and a flow sensor capable of measuring a flow rate of about 0 to about 800 liters per minute. It should be noted that inhalation flow rates are less than exhalation rates, e.g. max for inhalation 200 liters per minute and 800 liters per minute for exhalation. Various means to measure pressure differential related to air flow, such as a conventional measuring device in the air way, may be used. Further details regarding microprocessors are described within co-pending U.S. patent application entitled "An Automatic Aerosol Medication Delivery System and Methods", filed on Jan. 29, 1993 as patent application Ser. No. 08/002,507, which application is incorporated herein by reference in its entirety and specifically incorporated in order to describe and disclose flow measurements, the microprocessor and program technology used therewith.

Useful microprocessors include an external nonvolatile read/write memory subsystem, peripheral devices to support this memory system, reset circuit, a clock oscillator, a data acquisition subsystem and a visual annunciator subsystem. The discrete components are conventional parts which have input and output pins configured in a conventional manner with the connections being made in accordance with instructions provided by the device manufacturers. The microprocessor used to carry out the methodology of the invention is designed and programmed specifically so as to release drug within prescribed parameters as per FIG. 3, 4 and/or 5 and then repeatedly release at the same point to provide controlled and repeatable amounts of respiratory drug to a patient upon actuation. The microprocessor must have sufficient capacity to make calculations in real time. Adjustments can be made in the program so that when the patient's inspiratory flow profile is changed such may be taken into consideration. This can be done by allowing the patient to inhale through the device as a test (monitoring event) in order to measure air flow with preferred drug delivery points determined based on the results of several inhalations by each particular patient. This process can be readily repeated when the inspiratory flow profile is changed for whatever reason. When the patient's lung function has decreased the program will automatically back down in terms of the threshold levels required for release of drug. This "back down" function insures drug delivery to a patient in need but with impaired lung function. Determination of optimal drug delivery points in the inspiratory flow can be done at each dosing event, daily, weekly, or with the replacement of a new cellular array in the device.

The microprocessor, along with its associated peripheral devices, can be programmed so as to release drug any number of times within a given period of time. This feature makes it possible to prevent overdosing the patient. The overdose prevention feature can be particularly designed with each individual patient in mind or designed with particular groups of patients in mind. For example, the microprocessor can be programmed so as to prevent the release of more than approximately 200 μg of a given respiratory drug per day when the patient is normally dosed with approximately 100 μg of drug per day. The device can be designed to switch off this lock-out function so that drug can be delivered in an emergency situation.

The systems can also be designed so that only a given amount of a particular drug such as a respiratory drug is provided at a given dosing event. For example, the system can be designed so that only approximately 10 μg of respiratory drug is given in a given 15-minute period over which the patient will make approximately 10 inhalations with 1 μg of drug being delivered with each inhalation. By providing this feature, greater assurances are obtained with respect to delivering the respiratory drug gradually over time and thereby providing relief from the symptoms of respiratory disease without overdosing the patient.

The microprocessor of the invention can be connected to external devices permitting external information to be transferred into the microprocessor of the invention and stored within the non-volatile read/write memory available to the microprocessor. The microprocessor of the invention can then change its drug delivery behavior based on this information transferred from external devices. The methodology of invention is preferably provided in a portable, programmable, battery-powered, hand-held device for out-patient use. The device preferably has a size which compares favorably with existing metered dose inhaler devices and is less than 0.5 Kg in weight.

The microprocessor of the present invention is programmed so as to allow for monitoring and recording data from the inspiratory flow monitor without delivering drug. This is done in order to characterize the patient's inspiratory flow profile in a given number of monitoring events, which monitoring events preferably occur prior to dosing events. After carrying out a monitoring event, the preferred point within the inspiratory cycle for drug delivery can be calculated. This calculated point is a function of measured inspiratory flow rate as well as calculated cumulative inspiratory flow volume. This point is inside the parameters of FIGS. 3, 4 and 5 and once selected is used repeatedly. It is preferably a point which will occur often for that patient. This information is stored and used to allow activation of the electronic actuation means when the inhalation cycle is repeated during the dosing event. Although drug will always be released within the specifically indicated valves with respect to flow and volume, adjustments inside those parameters can be made to the optimize repeatability of dosing and the percentage of drug delivered to a particular patient.

Creating Aerosols

In order for any aspects of the present invention to be utilized an aerosol must be created. In a preferred embodiment formulation is initially forced through the pores of the porous membrane the formulation forms streams which are unstable and will, do to factors such as surface tension, break up into droplets on their own. The size of the droplets will be affected by factors such as the pore size, temperature, viscosity and the surface tension of the formulation forced through the pores. With some formulations the size of the particles within the dispersion may vary over a range and may include a large number of particles which are too large to be readily inhaled. If such occurs not all the drug can effectively enter the lungs for intrapulmonary delivery to have the desired effects. This problem can be solved by breaking the streams of liquid into particles having a diameter which are sufficiently small such that the patient can inhale the particles into the pulmonary tree. Although the particle size will vary depending on factors such as the particular type of formulation being aerosolized, in general, the preferred particle size is in the range of about 0.5 micron to about 12 microns. In order to obtain small particle sizes sufficient to aerosolize a formulation a number of different porous membranes and vibrating devices can be utilized as described in U.S. patent application entitled: "Systems For The Intrapulmonary Delivery Of Aerosolized Aqueous Formulations", filed May 20, 1994, as patent application Ser. No. 08/247,012.

Aerosols can be formed when pharmaceutical formulations in containers are forced through tiny openings (pores) in a polycarbonate or polyester membrane while the liquid, container and/or openings are simultaneously subjected to vibration. By vibrating at a particular frequency it is possible to form extremely small particles and create a fine mist aerosol. The particle size is determined by the size of the openings on the porous structure through which the liquid formulation is forced, the rate at which the fluid is forced from the container, and vibration frequency. More specifically, the aerosol particle size is a function of the diameter of the openings or pores through which the formulation is forced, vibration frequency, viscosity, liquid surface tension, and pressure at which liquid is extruded through the membrane. In essence, the particle size diameter will be approximately twice the pore size diameter with a margin of error of approximately ±20% or less. For example, if the membrane used includes pores having a diameter of 2 microns the aerosolized particles formed will have a size of approximately 3.6 to 4.4 microns in diameter. This relationship between particle size and pore diameter appears to hold over a pore sized diameter of approximately 0.5 micron to about 50 microns. Accordingly, it is possible to use membranes with pores therein having pore sizes of sufficient diameter to form aerosols having a particle sized diameter of about one micron to about 100 microns—although preferred particles have a diameter of about 0.5 to 12 microns. Different types of membrane materials can be used in connection with the invention. In general, the membrane will have a density of about 0.25 to about 3.0 mg/cm$^2$, more preferably about 1.7 mg/cm$^2$ and a thickness in the range of from about 2 to about 50 μm, more preferably about 14 to 16 μm. The membrane will cover the entire opening through which drug is forced and the opening will generally be in the form of an elongated rectangle. However, the size and the shape of the opening can vary and will generally have an area in the range of about 1.0 mm$^2$ to about 1.0 cm$^2$ but more preferably about 0.05–0.2 cm$^2$.

It is possible to create a "monodisperse" aerosol wherein all the particles within the aerosol created have essentially the same particle size. By adjusting parameters such as the surface tension of the formulation, pore hole size, and the air flow speed the size of the monodispersed particles can be adjusted within a very narrow range of size e.g. the particles will have a size diameter equal to each other with a margin of error of approximately ±10% or less, more preferably ±5% or less.

When small aerosolized particles are forced into the air, the particles encounter substantial frictional resistance. This causes the particles to slow down quickly and may result in particles colliding into each other and combining, which is undesirable with respect to maintaining the preferred particle size distribution within the aerosol. In order to aid in avoiding the particle collision problem, it is preferable to release drug along with an air flow directed toward the patient and away from the drug release nozzle opening. The air carries the formed particles along and aids in preventing their collision with each other. The amount of air flow needed will vary depending upon the amount of aerosol being formed. However, the amount of gas is generally five to two hundred times the volume of the liquid formulation within the container. Further, the flow velocity of the gas is generally about equal to the flow velocity of the aerosolized particles being forced from the nozzle. The shape of the container opening, the shape of the membrane covering that opening, as well as the positioning and angling of the gas flow and particle flow can be designed to aid in preventing particle collision. When the two flow paths are substantially parallel, it is desirable to shape the opening and matching membrane so as to minimize the distance between any edge of the opening and the center of the opening. Accordingly, it is not desirable to form a circular opening which would maximize the distance between the outer edges of the circle and the center of the circle, whereas it is desirable to form an elongated narrow rectangle. Using such a configuration makes it possible to better utilize the air flow relative to all of the particles being forced from a container. When a circular opening is used, particles which are towards the center of the circle may not be carried along by the air being forced from the openings and will collide with each other. The elongated rectangle could be formed in a circle, thereby providing an annular opening and air could be forced outward from the outer and inner edges of the circle formed.

Method of Administration

The method and device of the invention provides a number of features which make it possible to achieve the controlled and repeatable dosing procedure required for the treatment of diseases, particularly respiratory diseases such as asthma while maximizing the percentage amount of drug delivered to a patient.

The actuation method requires the use of a mechanism which causes drug to be forced from a container be fired automatically upon receipt of a signal from a microprocessor programmed to send a signal based upon data received from a measuring device (via a microprocessor) such as an airflow rate monitoring device. A patient using the device withdraws air from a mouthpiece and the inspiratory rate, and calculated inspiratory volume of the patient is measured simultaneously one or more times in a monitoring event which determines an optimal point in an inhalation cycle for the release of a dose of any desired drug. Inspiratory flow is preferably measured and recorded in one or more monitoring events for a given patient in order to develop an inspiratory flow profile for the patient. Recorded information is preferably analyzed by the microprocessor in order to deduce a preferred point within the patient's inspiratory cycle for the release of drug with the preferred point being calculated based on the most likely point to result in a reproducible delivery event.

A flow rate monitoring device continually sends information to the microprocessor, and when the microprocessor determines that the optimal point in the respiratory cycle is reached, the microprocessor actuates a component which causes drug to be forced out of the container and aerosolized. Accordingly, drug is always delivered at a preprogrammed place in the inspiratory flow profile of the particular patient which is selected specifically to maximize reproducibility of drug delivery and peripheral deposition of the drug.

The combination of automatic control of the drug release mechanism, combined with frequent monitoring events in order to calculate the optimal flow rate and time for the release of respiratory drug, combine to provide a repeatable means of delivering drug to the lungs of a patient in an efficient manner. Because the drug release mechanism is fired automatically and not manually, it can be predictably and repeatedly fired at that same point in the inspiratory cycle. Because dosing events are preferably preceded by monitoring events, the point in the inspiratory cycle of the release can be readjusted (within the parameters of FIG. 3) based on the particular condition of the patient. For example, patients suffering from asthma have a certain degree of pulmonary insufficiency which may well change with the administration of drug. These changes will be taken into account in the monitoring event by the microprocessor which will readjust the point of release of the respiratory drug in a manner calculated to provide for the administration of an amount of respiratory drug to the patient presently needed by the patient at each dosing event.

The entire dosing event can involve the administration of anywhere from 10 µg to 1,000 mg of drug formulation, but more preferably involves the administration of approximately 50 µg to 10,000 µg of drug formulation. This amount of drug is in a liquid form or is dissolved or dispersed within a pharmaceutically acceptable, liquid, excipient material to provide a liquid, flowable formulation which can be readily aerosolized. The container will include the formulation having drug therein in an amount of about 10 µl to 300 µl, more preferably about 200 µl. The large variation in the amounts which might be delivered are due to different drug potencies and different delivery efficiencies for different devices. The entire dosing event may involve several inhalations by the patient with each of the inhalations being provided with drug from the device. For example, the device can be programmed so as to release the contents of a single container or to move from one container to the next on a package of interconnected containers. Delivering smaller amounts from several containers can have advantages. Since only small amounts are delivered from each container and with each inhalation, even a complete failure to deliver drug with a given inhalation is not of great significance and will not seriously disturb the reproducibility of the dosing event. Further, since relatively small amounts are delivered with each inhalation, the patient can safely administer a few additional micrograms of drug (or milligrams for some drugs) without fear of overdosing.

In addition to drug potency and delivery efficiency, drug sensitivity must be taken into consideration. The present invention makes it possible to vary dosing over time if sensitivity changes and/or if user compliance and/or lung efficiency changes over time.

Based on the above, it will be understood that the dosing or amount of drug (and in particular respiratory drug) actually released from the device can be changed based on the most immediately prior monitoring event wherein the inspiratory flow of a patient's inhalation is measured.

Variations in doses are calculated by monitoring the effect of one or more lung function parameters in response to known amounts of respiratory drug released from each container and delivered to the patient. If the response in changing measured lung function parameters is greater than with previous readings, then the dosage (number of containers released) is decreased or the minimum dosing interval is increased. If the response in changing measured lung function parameters is less than with previous readings, then the dosing amount is increased or the minimum dosing interval is decreased. The increases and decreases are gradual and are preferably based on averages (of 10 or more readings of lung function parameter after 10 or more dosing events) and not a single dosing event and monitoring event. The method of the invention may further involve recording dosing events and lung function parameters over time, calculating averages and deducing preferred changes in administration of respiratory drug.

One of the important features and advantages of the present invention is that the microprocessor can be programmed to take different criteria into consideration with respect to dosing times. Specifically, the microprocessor can be programmed so as to include a minimum time interval between doses i.e. after a given delivery another dose cannot be delivered until a given period of time has passed. Secondly, the timing of the device can be programmed so that it is not possible to exceed the administration of a set maximum amount of drug within a given time. For example, the device could be programmed to prevent dispersing more than 200 μg (or two 100 μg containers of drug) of a particular drug within one hour. More importantly, the method may involve taking both criteria into consideration. Thus, the method can involve calculation of a minimum time interval between doses and a maximum amount of drug to be released within a given time period. For example, the microprocessor could be programmed to allow the release of a maximum of 200 μg of a given drug during an hour which could only be released in amounts of 25 μg with each release being separated by a minimum of five minutes.

The dosing program can be designed with some flexibility. For example, if the patient normally requires 250 μg per day of respiratory drug, the microprocessor of the inhalation device can be programmed to provide a warning after 250 μg have been administered within a given day and to continue the warning thereafter to alert the user of possible overdoses. By providing a warning and not a lock-out, the device allows for the patient to administer additional respiratory drug, if needed, due to a decreased lung function and/or account for misdelivery of respiratory drug such as due to coughing or sneezing during an attempted delivery.

Information regarding dosing with drugs can be found within Harrison's—Principles of Internal Medicine (most recent edition) and the Drug Evaluation Manual, 1993 (AMA-Division of Drugs and Toxicology), both of which are published by McGraw Hill Book Company, New York, incorporated herein by reference to disclose conventional information regarding dosing of drugs and in particular respiratory drugs as well as other useful drugs and formulations.

Supplemental Treatment Methodology

The methodology of the present invention can be used to deliver many types of drugs including drugs which have a systemic effect (e.g. narcotics, proteins such as DNAse and antibiotics) as well as drugs which have a local effect primarily on the lungs (e.g. bronchodilators). Because the present invention allows drug delivery directly to the lungs there are certain advantages with respect to using the invention for the delivery of drugs to treat respiratory diseases. However, the invention is not limited to respiratory drugs and specifically includes the delivery of drugs having a systemic effect. This is true also with respect to the supplemental treatment methodology described below even though this methodology is described with specific reference to respiratory diseases being treated with respiratory drugs.

Patients suffering from a given disease such as a respiratory disease may be treated solely with respiratory drug as indicated above, i.e. by intrapulmonary delivery. However, it is possible to treat such patients with a combination of intrapulmonary delivery and other means of administration such as oral administration. The oral drug is preferably given in amounts so as to maintain a baseline level of drug within the circulatory system which is sufficient to maintain body functions such as lung function at an acceptable level. However, this baseline level of drug to blood ratio (or serum blood level) must be raised in order to improve the body function such as lung function during periods of stress such as respiratory difficulty such as an asthma attack and such can be accomplished by the intrapulmonary administration of a drug such as a respiratory drug using the present invention.

Based on the above, it will be understood by those skilled in the art that a plurality of different treatments and means of administration can be used to treat a single patient. For example, a patient can be simultaneously treated with respiratory drug by transdermal administration, respiratory drug via intrapulmonary administration in accordance with the present invention, and drugs which are orally administered.

The instant invention is shown herein in what is considered to be the most practical and preferred embodiments. It is recognized, however, that departures may be made therefrom which are within the scope of the invention and that obvious modifications will occur to one skilled in the art upon reading this disclosure.

What is claimed is:

1. A method of drug delivery into a patient's airway, comprising:

simultaneously measuring a patient's inspiratory flow rate and inspiratory volume; determining whether the measured inspiratory flow rate and inspiratory volume equals a predetermined inspiratory flow rate and inspiratory volume; and releasing an aerosolized drug responsive to said measured inspiratory flow rate and inspiratory volume being determined to be equal to said predetermined inspiratory flow rate and inspiratory volume into the patient's inspiratory flow at substantially zero velocity at a point of release or at a velocity which reduces to substantially zero after travelling 2 cm or less from a point of release in the absence of the patient's inspiration.

2. The method of claim 1 wherein the inspiratory flow rate is in the range of from about 0.2 to about 1.8 liters/second and the inspiratory volume is in the range of from about 0.15 to about 0.40 liters.

3. The method of claim 1, wherein the inspiratory flow rate is in the range of from about 0.15 to about 1.8 liters/second and the inspiratory volume is in the range of from about 0.15 to about 0.25 liters.

4. The method of claim 1 wherein the aerosolized drug has a particle size in the range of from about 0.5 to 12 microns and wherein the drug is released at a velocity of substantially zero relative to the patient's inspiratory flow path.

5. The method of claim 1, wherein the measuring and releasing are carried out during a single inhalation of the patient.

6. The method of claim 1 wherein the aerosolized drug is in the form of aerosolized particles of a solution.

7. The method of claim 6, wherein the solution is an aqueous solution.

8. The method of claim 6, wherein the solution is comprised of drug dissolved in a low-boiling point propellant.

9. The method of claim 1, wherein the aerosolized drug is in the form of aerosolized particles of a suspension.

10. The method of claim 9, wherein the suspension is an aqueous suspension.

11. The method of claim 9, wherein the suspension is comprised of drug suspended in a low-boiling point propellant.

12. The method of claim 1, wherein the aerosolized drug is in the form of aerosolized particles of a dry powder.

13. The method of claim 1, wherein the measuring is carried out via electronic air flow measurement components.

14. The method of claim 1, wherein the measuring is carried out via mechanical air flow measurement components.

15. The method of claim 1, wherein the releasing is begun while the inspiratory flow rate is in the range of from about 0.10 to about 2.0 liters/second and the inspiratory volume is in the range of about 0.15 to about 0.80 liters and the releasing is completed outside the range of inspiratory flow rate of about 0.10 to about 2.0 liters/second.

16. The method of claim 1, wherein the releasing is begun while the inspiratory flow rate is in the range of from about 0.10 to about 2.0 liters/second and the inspiratory volume is in the range of about 0.15 to about 0.80 liters and the releasing is completed at an inspiratory volume of above about 0.40 liters.

17. The method of claim 1, wherein the releasing is begun and completed while the inspiratory flow rate is in the range of from about 0.10 to about 2.0 liters/second.

18. The method of claim 17, wherein the releasing is begun and completed while the inspiratory volume is in the range of about 0.15 to about 0.40 liters.

19. The method of claim 1, wherein aerosolized drug is released when the inspiratory flow rate is in a range of from about 0.10 to 2.0 liters/second and the patient's inspiratory volume is in a range of from about 0.15 to about 0.80 liters.

20. The method of claim 1, wherein the aerosolized drug is released at a therapeutically relevant inspiratory flow rate value above about 0.10 liters/second and inspiratory volume value above about 0.15 liters.

21. A method of drug delivery, comprising:

simultaneously measuring a patient's inspiratory flow rate and inspiratory volume with a portable, hand-held, battery-powered device; and releasing particles of a pharmaceutically active drug having a particle size in the range of from about 0.5 to 12 microns, the drug being released at a substantially zero rate of velocity relative to the patient's inspiratory flow path and occurring when the patient's measured inspiratory flow rate is in the range of from about 0.10 to 2.0 liters/second and the patient's inspiratory volume is in the range of from about 0.15 to about 0.80 liters.

22. The method of claim 21, wherein the releasing is begun within the inspiratory flow rate of about 0.10 to 2.0 liters/second and the inspiratory volume of about 0.15 to about 0.40 liters.

23. The method of claim 21, wherein the aerosolized drug is a pharmaceutically active respiratory drug.

24. The method of claim 21, wherein the aerosolized drug is a pharmaceutically active systemic drug.

25. The method of claim 21, wherein the aerosolized drug is asteroid selected from the group consisting of beclomethasone dipropionate, flunisolide, fluticasone, budesonide and triamcinolone acetonide.

26. The method of claim 21, wherein the aerosolized drug is a non-steroidal, anti-inflammatory drug.

27. The method of claim 21, wherein the aerosolized drug is selected from the group consisting of isoproterenol, cromolyn sodium, albuterol sulfate, metaproterenol sulfate, salmeterol xinafoate and formotorol.

28. The method of claim 21, wherein the particles have the same size within a range of ±20%.

29. The method of claim 28, wherein the particles have the same size within a range of ±10%.

30. The method of claim 29, wherein the particles have the same size within a range of ±5%.

* * * * *